United States Patent [19]

White

[11] Patent Number: 4,722,870

[45] Date of Patent: Feb. 2, 1988

[54] METAL-CERAMIC COMPOSITE MATERIAL USEFUL FOR IMPLANT DEVICES

[75] Inventor: Eugene W. White, Rossiter, Pa.

[73] Assignee: Interpore International, Irvine, Calif.

[21] Appl. No.: 692,978

[22] Filed: Jan. 22, 1985

[51] Int. Cl.[4] .......................... B32B 5/32; B32B 7/00; B22D 19/02; A61F 2/28

[52] U.S. Cl. ............................ 428/621; 428/539.5; 164/111; 623/16

[58] Field of Search ...................... 164/98, 111; 3/1.9, 3/1.91, 1.911, 1.912, 1.913; 264/19; 428/544, 304.4, 307.7, 312.8, 409, 687, 539.5; 433/201; 623/16

[56] References Cited

U.S. PATENT DOCUMENTS

| | | | |
|---|---|---|---|
| 3,058,216 | 10/1962 | Cohen | 264/19 |
| 3,314,420 | 4/1967 | Smith et al. | 128/92 |
| 3,605,123 | 9/1971 | Hahn | 3/1 |
| 3,713,860 | 1/1973 | Auskern | 117/8.5 |
| 3,855,638 | 12/1974 | Pilliar | 3/1 |
| 3,890,107 | 6/1975 | White | 428/613 |
| 3,929,971 | 12/1975 | Roy | 128/92 C |
| 3,934,347 | 1/1976 | Lash et al. | 32/10 A |
| 4,046,858 | 9/1977 | Barsa et al. | 3/1.9 |
| 4,127,902 | 12/1978 | Homsy | 3/1 |
| 4,131,597 | 12/1978 | Bluethgen et al. | 260/42.18 |
| 4,145,764 | 3/1979 | Suzuki et al. | 623/16 |
| 4,146,936 | 4/1979 | Aoyagi et al. | 3/1.91 |
| 4,149,894 | 4/1979 | Ebihara et al. | 3/1.9 |
| 4,164,794 | 8/1979 | Spector et al. | 3/1.9 |
| 4,168,326 | 9/1979 | Bruemer et al. | 3/1.9 |
| 4,192,021 | 3/1980 | Deibig et al. | 3/1.9 |
| 4,195,366 | 4/1980 | Jarco et al. | 3/1.9 |
| 4,222,128 | 9/1980 | Tommaga et al. | 623/16 |
| 4,223,412 | 9/1980 | Aoyagi et al. | 3/1.9 |
| 4,234,972 | 11/1980 | Hench et al. | 623/16 |
| 4,255,820 | 3/1981 | Rothermel et al. | 3/1 |
| 4,309,488 | 1/1982 | Heide et al. | 428/547 |
| 4,330,514 | 5/1982 | Nugai et al. | 3/1.9 |
| 4,366,183 | 12/1982 | Ghommidh et al. | 427/2 |
| 4,373,217 | 2/1978 | Draenert | 3/1.9 |
| 4,404,262 | 9/1983 | Watmough | 164/98 |
| 4,437,913 | 3/1984 | van der Zel et al. | 3/1.9 |
| 4,451,235 | 5/1984 | Okuda et al. | 433/201 |
| 4,492,577 | 1/1985 | Farris et al. | 433/201 |
| 4,547,327 | 10/1985 | Bruins et al. | 264/19 |
| 4,547,390 | 10/1985 | Ashman et al. | 427/2 |
| 4,599,085 | 7/1986 | Reiss et al. | 623/16 |
| 4,610,693 | 9/1986 | Niwa et al. | 623/16 |

FOREIGN PATENT DOCUMENTS

| | | | |
|---|---|---|---|
| 2400134 | 7/1974 | Fed. Rep. of Germany | 623/166 |
| 2659591 | 7/1977 | Fed. Rep. of Germany | 3/1.9 |
| 2821354 | 11/1978 | Fed. Rep. of Germany | 3/1.9 |
| 1359096 | 3/1964 | France | 623/160 |
| 26667 | 3/1981 | Japan | 164/98 |

OTHER PUBLICATIONS

Dunn, E. et al., "Replacement of the Canine Femoral Diaphysis with a Porous Coated Prosthesis", John Hopkins Medical J. 145, 101–106 (1979).

Ducheyne, P. et al., "Effect of Hydroxyapatite Impregnation on Skeletal Bonding of Porous Coated Implants", J. Biomed. Mat. Res. 14, 225–237 (1980).

Ducheyne, P. et al., "In Vivo Surface Activity of a Hydroxyapatite Alveolar Bone Substitute", J. Biomed. Mat. Res. 15, 441–445 (1981).

Fujiu, T. et al., "Difference of Bond Bonding Behavior Among Surface Active Glasses and Sintered Apatite", J. Biomed. Mat. Res. 18, 845–859 (1984).

Feenstra, C. et al., "Medical Use of Calcium Phosphate Ceramics", Bioceramics of Calfium Phosphate (CRC Press 1983), p. 131.

Hirschhorn, J. et al., "Powder Metallurgy Fabrication of Cobalt Alloy Surgical Implant Materials", *Research in Dental and Medical Materials* (Plenum Press, New York, 1979) (Ed. E. Korostaff).

Hulbert, S., "Materials of Construction for Surgical Implants", *South Carolina Engineer*, 19, 32–40 (1968).

Hahn, H. et al., "Preliminary Evaluation of Porous Metal Surfaced Titanium for Orthopedic Implants", J. Biomed. Mat. Res. 4, 571–577 (1970).

Jarcho, M. et al., "Tissue, Cellular, and Subcellular Events at a Bone–Ceramic Hydroxyapatite Interface", *J. Bioeng.*, 1, 79–92 (1977).

Jarcho, M., "Calcium Phosphate Ceramics as Hard Tissue Prosthetics", *Clinical Orthopaedics and Related Research* 157, 259–278 (1981).

Tracy, B. et al. "Direct Electron Microscopy Studies of the Bone–Hydroxyapatite Interface", J. Biomed. Mat. Res. 18, 719–726 (1984).

Weber, J. et al., "Carbonate Minerals as Precursors of New Ceramic, Metal, and Polymer Materials for Biomedical Applications", Miner. Sci. Engng. 5, 151–165 (1973).

*Primary Examiner*—John J. Zimmerman
*Attorney, Agent, or Firm*—Lyon & Lyon

[57] ABSTRACT

A material useful as a biomaterial for the manufacture of prosthetic devices and the like is provided by casting a suitable metal, such a Vitallium, into a hydroxyapatite and/or whitlockite investment with three-dimensional interconnected porosity. The resulting composite is finished to expose the investment in order to provide a superior surface for attachment to bone. The composite may be cast as part of the casting of metal prostheses such as hip joints or artificial teeth, in such a way that the investment is present in a thin layer at the desired bone attachment locations.

34 Claims, No Drawings

METAL-CERAMIC COMPOSITE MATERIAL USEFUL FOR IMPLANT DEVICES

FIELD OF THE INVENTION

This invention relates to the production of metal/ceramic composite materials. More particularly, this invention concerns composite materials that are useful as biomaterials, such as for the manufacture of prosthetic surgical and dental devices, bone implants and the like.

BACKGROUND OF THE INVENTION

As proportionally more people with remaining life expectancies longer than about 10 years become recipients of total hip and knee implant prostheses, long-term mechanical stability of these devices becomes increasingly important. Cements used to hold the intermedullary shafts in place, such as methylmethacrylate, tend to loose with time, and the use of screws or simple press-fitting often leads to implant failure over time. A variety of alternatives to these common fixation methods are being tried. These include: (1) coarse textured surfaces, (2) welded or sintered onlays of metal beads or wires, (3) surfaces with three-dimensional interconnected porosity, and (4) ceramic coatings such as calcium phosphates or alumina. Efforts are also underway to develop permanent implantable teeth and other prosthetic devices that also require fixation to bone.

Grooves and other surface relief features achieve fixation by bone growth into them thus providing a mechanical stabilization of the device without necessarily achieving a true bone-to-prosthesis bond.

Sintered porous onlays such as beads or crimped wire are meant to allow bone tissue ingrowth thus forming a better bonding action than simple grooves, etc. Bone tissue can ingrow porous metal surfaces but the ingrown bone tissue has a strong tendency to necrose and resorb in a period of many months or a few years. Evidently, the mechanical stresses necessary for maintaining healthy bone are not adequately transmitted into the rigid metal porosity. Another problem has to do with crevice corrosion occurring at any weld surface. Even slight chemical difference due to flux, etc., at a weld can promote galvanic corrosion when placed in contact with the body's electrolytes over a long time.

Both the textured surface approach and the sintered porous onlays present major problems in the event a prostheses has to be removed.

Prostheses in which the intermedullary shaft surfaces are metallic with three-dimensional interconnected porosity, have been achieved by the casting of metal into sintered coral sleeves. The sintered coral (composed of calcium oxide, CaO) is subsequently removed with etching by a mild acid, leaving a complementary negative of the original porous structure of the sintered coral. Dunn et al. [Johns Hopkins Med. J. 145, 101 (1979)] have shown that prostheses prepared in this manner achieved some success when implanted into mongrel dogs, resulting in firm attachment by bony ingrowth. These prostheses, however, faced the same problems noted above for textured surfaces and porous onlays, i.e., showing some evidence of necrosis/resorbtion of ingrown bone tissue.

Ceramic coatings on metal prostheses offer promise because they may permit true bone-to-prosthesis bonding but have to maintain ceramic/metal interface integrity for many years.

SUMMARY OF THE INVENTION

The present invention is directed to new metal/ceramic composite materials, their method of fabrication, and prosthetic devices incorporating new metal/ceramic composites. These new materials offer a superior solution to long term fixation of metal prostheses to bone.

The metal/ceramic composite materials are prepared by casting metal into a ceramic investment that has three-dimensional interconnected porosity, thus permitting the molten metal to freely penetrate the entire ceramic investment. The resulting composite is a solid, sturdy, and uniform material with a microstructure composed of two three-dimensional interconnecting and interwoven domains: one metal and one ceramic. The ceramic will be exposed at the surface of the composite material where needed for encouraging bony growth and attachment when the composite is used in an orthopedic or dental prosthesis capacity.

The ceramic employed may be any that is biocompatible, such as alpha alumina or cermet, but preferably should be of hydroxyapatite or hydroxyapatite/whitlockite mixture in order to best mimic the mineral composition of living bone for superior bone attachment. The three-dimensional interconnected porosity of the ceramic investment can be achieved in a number of ways.

The metal to be used should be biocompatible if the composite is to be incorporated into an implanted prosthesis.

The composite can form an entire prosthesis or be manufactured as a part of the process of casting an implantable prosthesis. In the latter application, the ceramic investment should be so located in the mold that the composite resulting after casting will be exposed in a thin layer at the surfaces of the prosthesis where bone attachment will be desired. Suitable finishing of the surface of the prosthesis will properly expose the composite so as to best encourage bone attachment.

Because the metal/ceramic surface—to which new bone will attach—is flush with the outer surface of the metal implant, removal of the device will be considerably easier than is the case for the mechanical fixation methods.

Thus, it is a primary purpose of the present invention to provide synthetic composite materials useful for biomaterials, such as for the manufacture of prosthetic devices and the like, and the method of making the same.

It is another object of this invention to provide a metal/ceramic composite material useful in the construction of surgical implantable prostheses.

A further object of the present invention is to provide a composite material which can be made as a sturdy, integral part of an implantable surgical prosthesis and facilitate long-term attachment of that prosthesis to bone without making the prosthesis overly difficult to remove should removal prove necessary.

Yet another object of the present invention is to provide a composite material for use in implantable surgical prostheses in order to provide superior fixation of the prosthesis to bone, and enhancing the long term mechanical and chemical stability of the prosthesis.

How these and other objects of this invention are achieved will become apparent in light of the accompanying disclosure.

DETAILED DESCRIPTION OF THE INVENTION

The metal/ceramic composite is made according to the present invention by casting a suitable metal into a suitable ceramic investment. The combination of the cast metal and the incorporated ceramic investment forms the composite. This composite may form an entire prosthesis, if used for that purpose, or form a part of a larger prosthesis and be situated at selected surfaces of that prosthesis. By suitable surface preparation, the ceramic investment will be exposed where bone attachment is desired.

The ceramic investment into which metal is cast has a three-dimensional interconnected porosity with relatively unconstricted channels, so that the molten metal can freely permeate that investment, and thus form a strong, solid, and reasonably uniform composite. The channels or pores must be of sufficient diameter that the molten metal is not overly impeded in its penetration during casting. Experience suggests that 50 microns is the minimum average channel size for effective centrifugal casting.

The three-dimensional interconnected porosity of the investment can be achieved in a number of ways. In the replamineform process, porous coral aragonite skeletons are hydrothermally converted to hydroxyapatite ($Ca_{10}(PO_4)_6(OH)_2$), as in the method disclosed by Roy (U.S. Pat. No. 3,929,971, filed Mar. 30, 1973, issued Dec. 30, 1975). The hydroxyapatite of the resulting material can be converted to a mixture of hydroxyapatite and whitlockite ($Ca_3(PO_4)_2$) by high temperature sintering (1250°–1400° C.). Other calcium phosphate compound materials with the requisite interconnected porosity may also be used to provide suitable hydroxyapatite or hydroxyapatite/whitlockite investments.

Suitable investments may also be prepared by making ceramic replicates in negative or positive form of the microstructure of marine invertebrate skeletal material, such as the coral Porites, in the manner disclosed by White et al. [U.S. Pat. No. 3,890,107, filed Sept. 25, 1972, issued June 17, 1975]. Such replicates can be made of alpha alumina or any other biocompatible ceramic.

The preferred ceramic materials for implant purposes are the calcium phosphates hydroxyapatite, hydroxyapatite/whitlockite mixtures, and whitlockite because these materials share chemical characteristics of the mineral component of living bone and are most compatible with bone regrowth and fixation. Hydroxyapatite is stable up to a temperature of approximately 1300° C. whereas hydroxyapatite/whitlockite mixture or pure whitlockite can resist higher temperatures, which may be necessary in casting certain metal with high melting point, such as titanium alloy. Hydroxyapatite and hydroxyapatite/whitlockite mixtures may not be suitable as investment material when titanium alloy is the metal to be cast, due to the high casting temperature of titanium alloy and its reactivity at such temperature. The process whereby a naturally occurring porous material, such as coral skeletal material, is converted into suitable calcium phosphates is the preferred method of obtaining the requisite interconnected porosity.

Any of a wide variety of metals could be cast into the investment, such as 316L stainless steel, chromium alloys, cobalt alloys, titanium alloys, silver alloys, gold alloys and the like when biocompatibility is desired. The chromium-cobalt-molybdenum alloy having the approximate composition 65% cobalt, 35% chromium and 5% molybdenum commonly called Vitallium is frequently used in the making of prosthetic devices by virtue of its biocompatability, and strength, and would be a good choice when the composite is to be used for implant purposes, such as implantable teeth and joint prostheses.

In the embodiment of the present invention in which the metal/ceramic composite forms substantially the entire prosthesis or object to be made, the following casting process is preferred.

A suitable sized and shaped piece of ceramic investment material is first impregnated with casting wax and excess wax removed from all surfaces. The wax-impregnated investment is then treated as would be any wax master used in lost wax casting. Thus, sprue wax is attached to the investment, sprue wax and investment are embedded in investment material such as Kerr Cristobalite Investment, and the wax is then melted and burned off, leaving the porous ceramic investment potted inside an outer mold with a sprue hole included. The combination of porous ceramic investment and outer mold forms the complete mold into which the metal is to be cast.

The complete mold is preheated and then the metal alloy cast. In the case of Vitallium, good results are obtained if the mold is preheated to 1150° C. and the Vitallium cast at 1568° C. The metal may be cast using standard centrifugal casting techniques. Casting in a vacuum or inert gas atmosphere would be preferable because it helps avoid the formation of oxides which would be detrimental to bone fixation and prosthesis-bone long term stability.

One cast and cooled, the outer mold is removed and the resulting metal/ceramic composite piece exposed. The composite is characterized by two interpenetrating or interconnected three-dimensional regions, one made of ceramic and one of metal alloy. Each region is a single, multiply interconnected domain with a generally fenestrate structure.

The surface of the piece may be ground, polished with diamond or carbide tools, and then cleaned. The ceramic will appear on the surface of the composite as a fine mosaic and thus is available on the surface of the piece where proper bone attachment is desired.

The exposed surface of the metal/ceramic composite may be lightly sandblasted, with an abrasive harder than the ceramic and softer than the metal alloy, in order to remove surface ceramic to a level of about 100 microns. This produces a finely pitted surface which encourages bone fixation without permitting the extensive bone ingrowth that could occur if the surface had a three-dimensional interconnected porosity available for such ingrowth. Sandblasting or other abrasive processes are preferred over etching with chemical solvents which may result in leaving unwanted compounds and residues which would interfere with bone fixation.

Yet another method of surface preparation requires an added step in the preparation of the ceramic investment. Selected surfaces of the investment which are to be available for bone attachment are filled with a fine powder such as calcium oxide, so that the pores or channels in the ceramic are clogged or blocked to a certain depth. The rest of the mold preparation process, as described above, proceeds as usual. During casting the fine powder prevents entry of the molten metal alloy into the pores of the investment at the selected surfaces. After casting the fine powder is removed by ultrasonic cleaning methods. The pores of the selected surface of the investment are then free of metal alloy to the depth filled by the powder. The selected surface then consists of the original ceramic investment with its interconnected porosity intact. Given a pore size large enough to permit bone ingrowth and osteon formation, such porosity is known to encourage exuberant bone ingrowth and superior fixation as a result, at least initially. The exposed ceramic investment is strongly attached to the underlying ceramic/metal composite by virtue of the integral construction of the ceramic investment.

While metal/ceramic composites undoubtedly have uses as implant parts in themselves, the most widely useful application likely will be as thin (for example, ½ to 5 millimeters) ceramic/metal surface layers or onlays on larger prosthetic devices, for the purpose of bone attachment and to achieve long term fixation. In this embodiment of the invention, wax-impregnated pieces of the porous ceramic are incorporated in the walls of an investment mold used to cast a given device. After burnoff of the wax, the casting is a one step procedure that would cast the device (total hip or knee joint, for example) and molten metal would be simultaneously injected also into the "onlay" regions. This one-shot casting procedure effects a non-weld porous onlay. Following the casting procedure, the device would be given a final grind and polish with diamond or carbide abrasive tools and cleaned. Properly finished as described above, the exposed hydroxyapatite would be available on the surface of the prosthesis at those regions where bone attachment was desired but would extend into the prosthesis only to a limited depth in order to not affect the strength and other mechanical qualities of the prosthesis.

The invention may be illustrated by description of the below example, without being limited thereto. This example demonstrates that hydroxyapatite can make an excellent investment material.

Rectangular block pieces of Interpore International replamineform hydroxyapatite, sold under the names Interpore 200 TM and Interpore 500 TM, were selected. Sizes ranged from ½" cubes to pieces 1×1×1½". Each piece was impregnated with casting wax in the following manner. The wax was melted at 105° C. Each preheated hydroxyapatite piece was suspended by cotton thread and lowered slowly into the molten wax. The hydroxyapatite (or hydroxyapatite/whitlockite) was wetted by the wax such that capillary forces "wicked" the wax one-half inch or so into the structure above the liquid wax level in the beaker. The wetted piece was slowly lowered into the wax and the wax allowed to cool until it had just started to solidify. The impregnated part was then pulled from the soft wax, thread removed and excess wax cleaned from all surfaces.

A centrifugal metal casting machine may be used for the casting. The castings of the present example were done by commercial laboratories according to industry standards.

The wax-impregnated hydroxyapatite parts were handled as regular wax masters would be handled for lost wax casting. Sprue wax was, thus, attached to the wax/hydroxyapatite composite piece, the piece potted in the usual investment material, the residual wax melted out and burned off, the molds preheated to 1150° C., and molten Vitallium cast at 1568° C.

The hydroxyapatite/Vitallium composites so produced were sliced with an abrasive saw and several surfaces polished. The metal had penetrated the porosity throughout and formed a good composite with only a few unfilled voids (5–10% unfilled). Microscopically, no evidence existed for any chemical reaction of the molten metal with the investment during the brief high temperature exposure. This is important for minimizing body uptake of metal ions that could more easily occur from any oxide compound formed at the metal/ceramic interface.

As will be apparent to those skilled in the art in light of the preceding disclosure, many modifications, alterations, substitutions and uses are possible in the practice of this invention without departing from the spirit or scope thereof.

What is claimed is:

1. A synthetic composite material, the structure of which is characterized by two interpenetrating three-dimensional regions, each of said regions being a single, multiply interconnected domain, one of said regions being composed of a metal and the other of said regions being composed of a calcium phosphate.

2. A material in accordance with claim 1 in which said calcium phosphate is hydroxyapatite.

3. A material is accordance with claim 1 in which said calcium phosphate is a mixture of hydroxyapatite and whitlockite.

4. A material in accordance with claim 1 in which said calcium phosphate is whitelockite.

5. A material in accordance with claim 1 in which said metal is an alloy comprising about 56% cobalt, about 35% chromium, and about 5% molybdenum.

6. A material in accordance with claim 1 in which said metal is stainless steel.

7. A material in accordance with claim 1 in which said metal is a cobalt alloy.

8. A material in accordance with claim 1 in which said metal is a titanium alloy.

9. A material in accordance with claim 1 in which said metal is a silver alloy.

10. A material in accordance with claim 1 in which said metal is a gold alloy.

11. A synthetic composite material useful as a biomaterial, the structure of which is characterized by two interpenetrating three-dimensional regions, each of said regions being a single multiple interconnected domain, one of said regions being composed of hydroxyapatite and the other of said regions being composed of a biocompatible metal.

12. A material in accordance with claim 11 in which said metal is selected from the group stainless steel, titanium alloy, cobalt alloy, an alloy comprising abut 65% cobalt, about 35% chromium, and about 5% molybdenum, silver alloy and gold alloy.

13. A synthetic composite material useful as a biomaterial, the structure of which is characterized by two interpenetrating three-dimensional regions, each of said regions being a single multiply interconnected domain, one of said regions being composed of a mixture of hydroxyapatite and whitlockite, and the other of said regions being composed of a biocompatible metal.

14. The material according to claim 13 in which said metal is selected from the group stainless steel, titanium alloy, cobalt alloy, an alloy comprising abut 65% cobalt, about 35% chromium, and about 5% molybdenum, silver alloy and gold alloy.

15. A synthetic composite material useful as a biomaterial, the structure of which is characterized by two interpenetrating three-dimensional regions, each of said regions being a single multiply interconnected domain, one of said regions being composed of whitlockite, and the other of said regions being composed of a biocompatible metal.

16. The material according to claim 15 in which said metal is selected from the group stainless steel, titanium alloy, cobalt alloy, an alloy comprising about 65% cobalt, about 35% chromium, and about 5% molybdenum, silver alloy and gold alloy.

17. A synthetic composite material useful as a biomaterial formed by the casting of a metal into a calcium phosphate investment, said calcium phosphate investment being characterized by a three-dimensional interconnected porosity and by being a single multiply interconnected domain.

18. A material in accordance with claim 17 in which the calcium phosphate of said calcium phosphate investment is hydroxyapatite and said metal is selected from the group stainless steel, titanium alloy, cobalt alloy, an alloy comprising about 65% cobalt, about 35% chromium, and about 5% molybdenum, silver alloy and gold alloy.

19. A material in accordance with claim 17 in which the calcium phosphate of said calcium phosphate investment is a hydroxyapatite/whitlockite mixture and said metal is selected from the group stainless steel, titanium alloy, cobalt alloy, an alloy comprising about 65% cobalt, about 35% chromium, and about 5% molybdenum, silver alloy and gold alloy.

20. A material in accordance with claim 17 in which the calcium phosphate investment is whitlockite and said metal is selected from the group stainless steel, titanium alloy, cobalt alloy, an alloy comprising 65% cobalt, about 35% chromium, and about 5% molybdenum, silver alloy and gold alloy.

21. An implantable surgical or dental prosthesis composed of a synthetic composite material, the structure of said composite material being characterized by two interpenetrating three-dimensional regions, each of said regions being a single multiple interconnected domain, one of said regions being composed of a calcium phosphate and the other of a metal.

22. An implantable surgical or dental prosthesis in accordance with claim 21 in which said calcium phosphate is hydroxyapatite and said metal is selected from the group stainless steel, titanium alloy, cobalt alloy, an alloy comprising 65% cobalt, about 35% chromium, and about 5% molybdenum, silver alloy and gold alloy.

23. An implantable surgical or dental prosthesis according to claim 22, in which said composite material forms only part of said prosthesis and is present at locations where bone fixation is desired, said composite material being exposed at the surface of said prosthesis at said locations.

24. An implantable surgical or dental prosthesis in accordance with claim 21 in which said calcium phosphate is a hydroxyapatite/whitlockite mixture and said metal is selected from the group stainless steel, titanium alloy, cobalt alloy, an alloy comprising about 65% of cobalt, about 35% chromium, and about 5% molybdenum, silver alloy and gold alloy.

25. An implantable surgical or dental prosthesis according to claim 24, in which said composite material forms only part of said prosthesis and is present at locations where bone fixation is desired, said composite material being exposed at the surface of said prosthesis at said locations.

26. An implantable surgical or dental prosthesis in accordance with claim 21 in which said calcium phosphate is whitlockite and said metal is selected from the group stainless steel, titanium alloy, cobalt alloy, an alloy comprising about 65% cobalt, 35% chromium, and about 5% molybdenum, silver alloy and gold alloy.

27. An implantable surgical or dental prosthesis according to claim 21, in which said composite material forms only part of said prosthesis and is present at locations where bone fixation is desired, said composite material being exposed at the surface of said prosthesis at said locations.

28. An implantable surgical or dental prosthesis according to claim 27, in which said composite material forms only part of said prosthesis and is present at locations where bone fixation is desired, said composite material being exposed at the surface of said prosthesis at said locations.

29. An implantable surgical or dental prosthesis according to claim 27 in which the surface of said composite material, exposed at said locations where bone fixation is desired, is pitted through selective removal of said calcium phosphate.

30. An implantable surgical or dental prosthesis according to claim 21 in which the surface of said composite material, exposed at said locations were bond fixation is desired, is pitted through selected removal of said calcium phosphate.

31. The process which comprises the steps of preparing a calcium phosphate investment for casting, said calcium phosphate investment having a three-dimensional, interconnected porosity and comprising a single multiply interconnected domain, casting molten metal into said investment, and allowing said metal to solidify so that a metal/calcium phosphate composite material results, and finishing a surface of said resulting metal/calcium phosphate composite material so that said calcium phosphate investment is exposed at said surface.

32. The process according to claim 31 in which the step of finishing comprises the steps of placing, prior to casting, a fine powder resistant to the heat of casting in said porosity of said calcium phosphate investment at a selected surface thereof, to a selected depth from said surface and removing said powder after the solidification of said metal.

33. The process according to claim 32 in which said fine powder is calcium oxide powder.

34. The process which comprises the steps of preparing a calcium phosphate investment for casting, said calcium phosphate investment having a three-dimensional interconnected porosity and comprising a single multiply interconnected domain, casting molten metal into said investment, allowing said metal to solidify so that a metal/calcium phosphate composite material results, finishing a surface of the resulting metal/calcium phosphate composite material so that said calcium phosphate investment is exposed at said surface, and pitting said surface through selective removal of said exposed calcium phosphate investment.

* * * * *